(12) United States Patent
Zerhusen et al.

(10) Patent No.: US 11,217,347 B2
(45) Date of Patent: Jan. 4, 2022

(54) SYSTEMS FOR PATIENT TURN DETECTION AND CONFIRMATION

(71) Applicant: Hill-Rom Services, Inc., Batesville, IN (US)

(72) Inventors: Mark Zerhusen, Cincinnati, OH (US); Bryan Weidman, Columbus, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 268 days.

(21) Appl. No.: 16/526,347

(22) Filed: Jul. 30, 2019

(65) Prior Publication Data
US 2020/0043607 A1    Feb. 6, 2020

Related U.S. Application Data

(60) Provisional application No. 62/713,178, filed on Aug. 1, 2018.

(51) Int. Cl.
| | |
|---|---|
| *G16H 40/63* | (2018.01) |
| *A61B 5/0205* | (2006.01) |
| *G16H 80/00* | (2018.01) |
| *A61B 5/021* | (2006.01) |
| *A61B 5/11* | (2006.01) |
| *G08B 21/04* | (2006.01) |

(52) U.S. Cl.
CPC .......... *G16H 40/63* (2018.01); *A61B 5/0205* (2013.01); *A61B 5/1115* (2013.01); *G08B 21/0423* (2013.01); *G08B 21/0461* (2013.01)

(58) Field of Classification Search
CPC ..................................................... G16H 40/63
See application file for complete search history.

(56) References Cited

U.S. PATENT DOCUMENTS

| | | | |
|---|---|---|---|
| 7,253,366 B2 | 8/2007 | Bhai | |
| 8,491,492 B2 | 7/2013 | Shinar et al. | |
| 9,358,168 B2 | 6/2016 | Williamson et al. | |
| 9,761,109 B2 | 9/2017 | Ribble et al. | |
| 2016/0022218 A1* | 1/2016 | Hayes | A61B 5/4809 600/301 |
| 2016/0166453 A1* | 6/2016 | Furman | A61G 7/015 700/275 |
| 2017/0004259 A1* | 1/2017 | Robinson | G16H 40/20 |
| 2017/0229149 A1* | 8/2017 | Rothschild | H04N 5/76 |
| 2020/0368491 A1* | 11/2020 | Poltorak | A61B 5/165 |

* cited by examiner

*Primary Examiner* — Joseph H Feild
*Assistant Examiner* — Pameshanand Mahase
(74) *Attorney, Agent, or Firm* — Dinsmore & Shohl LLP; Matthew D. Epstein (57) ABSTRACT

A system for detecting patient turns includes a person support apparatus including a person support surface and a support frame, a plurality of load cells for generating load cell data, a sensor for sensing at least one of heart rate data and respiration rate data for an individual, and a computing device coupled to the plurality of load cells and the sensor. The computing device receives the load cell data and the at least one of heart rate data and respiration rate data for the individual, detects that a patient turn has occurred on the person support surface based on the load cell data and the at least one of heart rate data and respiration rate data for the individual, and causes an indication that the patient turn occurred to be logged in an electronic medical record corresponding to the individual.

19 Claims, 7 Drawing Sheets

SYSTEMS FOR PATIENT TURN DETECTION AND CONFIRMATION

CROSS REFERENCE TO RELATED APPLICATIONS

The present application claims the benefit of U.S. Provisional Application Ser. No. 62/713,178 filed Aug. 1, 2018 and entitled "Systems For Patient Turn Detection And Confirmation," the entirety of which is incorporated by reference herein.

TECHNICAL FIELD

The present specification generally relates to systems for monitoring patient turns and, more particularly, systems for automatically determining that a patient has been turned and providing confirmation of patient turns.

BACKGROUND

In order to prevent pressure ulcers, conventional nursing practice provides for repositioning an individual approximately every two hours. The repositioning of the individual enables blood flow throughout the skin and reduces pressure on areas of the skin that, over time, would begin to break down. For some individuals, such as those individuals that are unable to move themselves, a caregiver may be responsible for repositioning the individual and recording the repositioning, or turn, in the individual's chart.

Given that the treatment of pressure ulcers are usually non-reimbursable patient care expenses under various insurance guidelines, administration and recordation of the turns is important to mitigate the occurrence of pressure ulcers in care facilities.

Accordingly, a need exists for systems that detect and confirm patient turns.

SUMMARY

According to some embodiments of the present disclosure, a system for detecting patient turns includes a person support apparatus including a person support surface and a support frame, a plurality of load cells for generating load cell data, a sensor for sensing at least one of heart rate data and respiration rate data for an individual, and a computing device coupled to the plurality of load cells and the mechanical sensor. At least one of the plurality of load cells is positioned at or proximate to each corner of the support frame. The sensor is disposed between the person support surface and the support frame. The computing device receives the load cell data and the at least one of heart rate data and respiration rate data for the individual. In particular, the computing device includes a processor and memory storing computer readable and executable instructions that, when executed by the processor, cause the computing device to detect that a patient turn has occurred on the person support surface based on the load cell data and the at least one of heart rate data and respiration rate data for the individual, and cause an indication that the patient turn occurred to be logged in an electronic medical record corresponding to the individual.

According to some embodiments of the present disclosure, a method for detecting patient turns includes receiving load cell data from a plurality of load cells positioned on a person support apparatus; receiving heart rate data and respiration rate data for an individual from a sensor coupled to the person support apparatus; determining that a waveform of the load cell data over a period of time is indicative of a possible patient turn; identifying at least one of a decrease in a respiration rate of the individual over the period of time and an increase in a heart rate of the individual over the period of time; determining that the patient turn occurred based on the determination that the waveform of the load cell data over a period of time is indicative of a possible patient turn and the identification of at least one of the decrease in the respiration rate and the increase in the heart rate of the individual over the period of time; and causing an indication that the patient turn occurred to be logged in an electronic medical record corresponding to the individual.

Additional features and advantages will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this specification. The drawings illustrate the various embodiments described herein, and together with the description serve to explain the principles and operations of the claimed subject matter.

BRIEF DESCRIPTION OF THE DRAWINGS

Referring now to the illustrative examples in the drawings, wherein like numerals represent the same or similar elements throughout.

DETAILED DESCRIPTION

Figure 1:
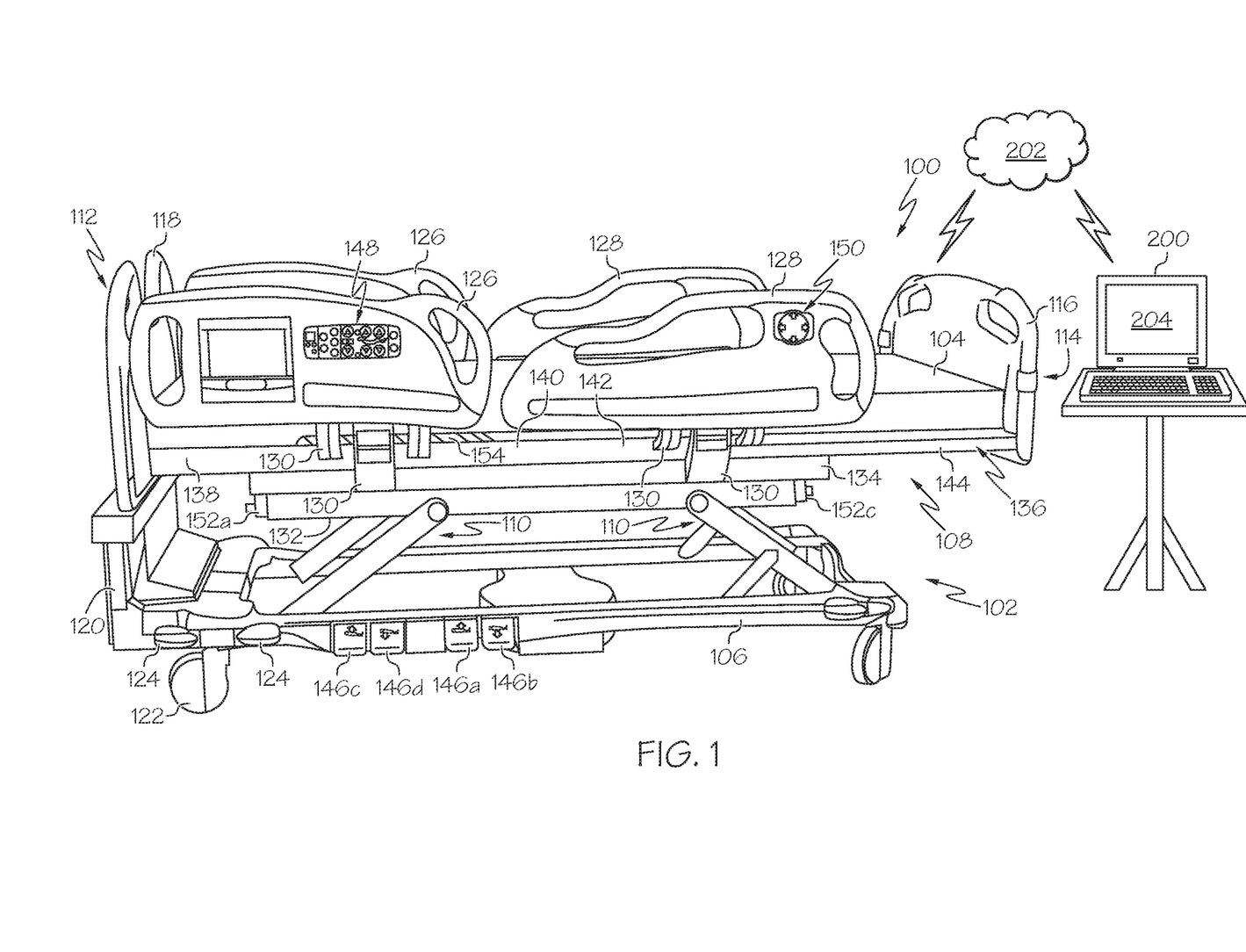
FIG. 1 is a perspective view of a person support apparatus according to one or more embodiments shown and described herein.

FIG. 1 generally depicts one embodiment of a person support apparatus for use in detecting patient turns. The person support apparatus includes a plurality of load cells and at least one mechanical sensor. The load cells provide load cell data that can be analyzed by a computing device to determine if a possible patient turn has occurred based on movement of an individual on the person support apparatus. The mechanical sensor senses heart rate data and/or respiration rate data of the individual. In embodiments, a computing device analyzes patterns in the heart rate data and/or the respiration rate data to determine if the possible patient turn occurred. Accordingly, the computing device can detect the occurrence of a patient turn based on the load cell data, the heart rate data, and/or the respiration rate data. Various embodiments of systems and methods for detecting patient turns will be described in more detail herein with specific reference to the appended drawings.

A person support apparatus 100 including a frame 102 and a person support surface 104 is shown in FIG. 1. The frame 102 includes a base 106, an upper frame assembly 108, and a lift system 110 coupling the upper frame assembly 108 to the base 106. The lift system 110 is operable to raise, lower, and tilt the upper frame assembly 108 relative to the base 106. The person support apparatus 100 has a head end 112 and a foot end 114, and further includes a footboard 116 at the foot end 114 and a headboard 118 at the head end 112 of the person support apparatus 100. The headboard 118 is coupled to an upstanding portion 120 of the base 106 at the head end 112 of the person support apparatus 100. The footboard 116 is coupled to the upper frame assembly 108. The base 106 includes wheels or casters 122 that roll along a floor (not shown) as the person support apparatus 100 is moved from one location to another. A set of foot pedals 124 is coupled to the base 106 and is used to brake and release the casters 122.

As shown in FIG. 1, the person support apparatus 100 has four siderail assemblies coupled to the upper frame assembly 108. The four siderail assemblies include a pair of head siderail assemblies 126 (sometimes referred to as head rails) and a pair of foot siderail assemblies 128 (sometimes referred to as foot rails). Each of the siderail assemblies 126, 128 is movable between a raised position, as shown in FIG. 1, and a lowered position (not shown). Siderail assemblies 126, 128 are sometimes referred to herein as siderails 126, 128. Each siderail 126, 128 includes a linkage 130 coupled to the upper frame assembly 108 and configured to guide the siderails 126, 128 between the raised and lowered positions.

The upper frame assembly 108 includes a lift frame 132, a weigh frame 134 supported with respect to the lift frame 132, and a person support deck 136. The person support deck 136 is carried by the weigh frame 134 and engages a bottom surface of the person support surface 104. The person support deck 136 includes a head section 138, a seat section 140, a thigh section 142, and a foot section 144, as shown in FIG. 1. In various embodiments, sections 138, 142, and 144 are each movable relative to the weigh frame 134. For example, the head section 138 may pivotally raise and lower relative to the seat section 140, the foot section 144 may pivotally raise and lower relative to the thigh section 142, and the thigh section 142 may articulate relative to the seat section 140. Additionally, in some embodiments, the foot section 144 may extend and retract to change the overall length of the foot section 144 and, therefore, to change the overall length of the person support deck 136.

In the embodiment depicted in FIG. 1, the seat section 140 is fixed in position with respect to the weigh frame 134 as the person support deck 136 moves between its various positions including a horizontal position (shown in FIG. 1) and a chair position (not shown). In other embodiments, the seat section 140 also moves relative to the weigh frame 134, such as by pivoting and/or translating. In such embodiments, the thigh and foot sections 142, 144 may also translate along with the seat section 140. In the chair position, the head section 138 extends upwardly from the weigh frame 134 and the foot section 144 extends downwardly from the thigh section 142.

Additionally, the person support apparatus 100 includes four foot pedals 146a, 146b, 146c, 146d coupled to the base 106. In embodiments, the foot pedals may be used to raise and lower portions of the person support apparatus 100. For example, foot pedal 146a may be used to raise the upper frame assembly 108 relative to the base 106, the foot pedal 146b may be used to lower the upper frame assembly 108 relative to the base 106, the foot pedal 146c may be used to raise the head section 138 relative to the weigh frame 134, and the foot pedal 146d may be used to lower the head section 138 relative to the weigh frame 134. In other embodiments, one or more of the foot pedals may be omitted, or additional foot pedals may be included.

In embodiments, each siderail 126 includes a first user control panel 148 coupled to the outward side of the siderail 126 and each siderail 128 includes a second user control panel 150 coupled to the outward side of the siderail 128. The control panels 148, 150 include various buttons that may be used by a caregiver to control associated functions of the person support apparatus 100. For example, the first user control panel 148 may include buttons that are used to operate a motor to raise and lower the head section 138, buttons that are used to operate a motor to raise and lower the thigh section 142, and buttons that are used to operate motors to raise lower, and tilt the upper frame assembly 108 relative to the base 106. The second user control panel 150 may include buttons that are used to operate a motor to raise and lower the foot section 144 and buttons that are used to operate a motor to extend and retract the foot section 144.

In various embodiments, one or more components of the person support apparatus 100 are coupled to a computing device 200, which is configured to sense and/or collect information from the components coupled thereto, process the information, and perform one or more actions based on the information. The computing device 200 may additionally provide various resources to the person support apparatus 100. Resources include providing, for example, processing, storage, software, and information from other systems in the facility to the person support apparatus 100. In various embodiments, as will be described in greater detail below, the computing device 200 can detect and/or confirm the occurrence of a patient turn based in information sensed or collected from various components of the person support apparatus 100. The components may be coupled wirelessly to the computing device 200, such as through a network 202, or the components may be coupled to the computing device 200 via wires. Accordingly, in some embodiments, one or more components of the person support apparatus 100 may include wireless communication circuitry, or be communicatively coupled to wireless communication circuitry incorporated into the person support apparatus 100 (not shown).

The computing device 200 may be any device having hardware (e.g., chipsets, processors, memory, etc.) for communicatively coupling with the network 202. Specifically, the computing device may be a mobile device, a desktop computing device, or a computing device incorporated into or attached to the person support apparatus 100, depending on the particular embodiment. For example, the computing device 200 may be a smart phone, a tablet device, an e-reader, a laptop computer, a desktop computer, or a computer associated with the person support apparatus 100. In various embodiments, the computing device 200 may be a device accessible by one or more caregivers, such as a computing device located at a nurses' station, in a doctor's office, or carried by the caregiver.

In various embodiments, the computing device 200 includes one or more non-transitory memory components, one or more processing devices, a display 204, a speaker, at least one input device, and network interface hardware. The one or more non-transitory memory components store computer readable and executable instructions that, when executed by the processor, cause the computing device 200 to perform one or more functions described herein. In particular, the one or more non-transitory memory components may store computer readable and executable instructions that, when executed by the processor, cause the computing device 200 to perform the functions of the various modules described hereinbelow, including but not limited to, analyzing data from one or more components of the person support apparatus 100, identifying a possible patient turn, confirming that a patient turn occurred, and/or causing an indication that the patient turn occurred to be logged in an electronic medical record corresponding to the individual. The at least one input device can include, by way of example and not limitation, a microphone, a keyboard, a touch screen, a mouse, or the like. The network interface hardware may depend on the particular embodiment, and may include the hardware to enable the computing device 200 to communicate via the network. The display can include any medium capable of transmitting an optical output such as, for example, a cathode ray tube, light emitting diodes, a liquid crystal display, a plasma display, or the like. Moreover, in some embodiments, the display is a touchscreen that, in addition to providing visual information, detects the presence and location of a tactile input upon a surface of or adjacent to the display. The computing device 200 may include additional or fewer components, depending on the particular embodiment. For example, in embodiments in which the computing device 200 is a smart phone, it may further include cellular network hardware and a microphone and not include a mouse, while in embodiments in which the computing device 200 is a desktop computing device, it may include a keyboard and a mouse and not include a touch screen.

In various embodiments, the computing device 200 is communicatively coupled to one or more input devices of the person support apparatus 100 that collect information indicative of the occurrence of a patient turn. For example, in various embodiments, the person support apparatus 100 may include load cells 152a-152d, mechanical sensors 154, or the like, that provide data to the computing device 200 which detects and/or confirms the occurrence of a patient turn based on the received data. Various input devices and methods for detecting and/or confirming the occurrence of a patient turn will now be described.

In various embodiments, the person support apparatus 100 further includes a number of load cells positioned between the weigh frame 134 and the base 106. Each load cell is configured to produce a voltage or current signal indicative of a weight impressed on that load cell from the weigh frame 134 relative to the base 106. In the embodiment shown in FIG. 1, four load cells 152a, 152b, 152c, and 152d are positioned between the weigh frame 134 and the base 106; one at or proximate to each corner of the person support apparatus 100, although only two of the load cells 152a and 152c can be seen in FIG. 1. However, all four load cells 152a, 152b, 152c, and 152d are shown in FIG. 2.

Some of the structural components of the person support apparatus 100 will be designated hereinafter as "right," "left," "head," and "foot" from the reference point of an individual lying on the individual's back on the person support surface 104 with the individual's head oriented toward the head end 112 of the person support apparatus 100 and the individual's feet oriented toward the foot end 114 of the person support apparatus 100. For example, the weigh frame 134 illustrated in FIG. 2 includes a head end weigh frame member 134c mounted to one end of a right side weigh frame member 134a and at an opposite end to one end of a left side weigh frame member 134b. Opposite ends of the right side weigh frame member 134a and the left side weigh frame member 134b are mounted to a foot end weigh frame member 134d. A middle weigh frame member 134e is mounted at opposite ends to the right and left side weigh frame members 134a and 134b, respectively, between the head end and foot end weigh frame members 134c and 134d.

Figure 2:
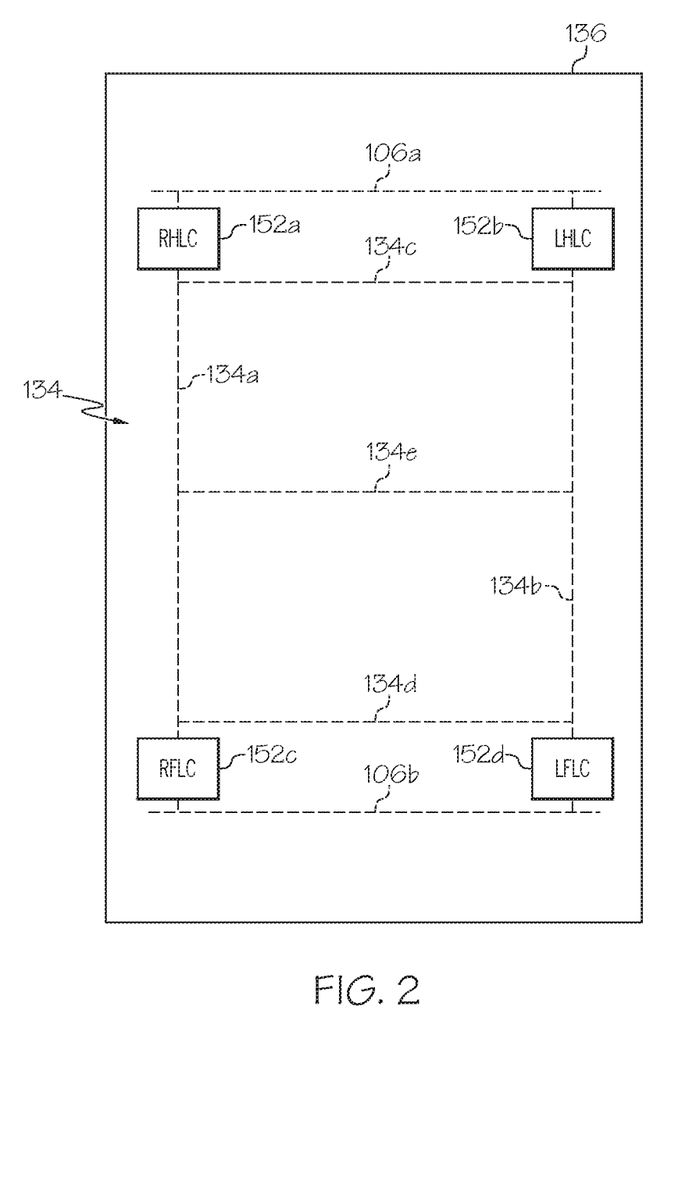
FIG. 2 is a block diagram illustrating locations of a number of load cells relative to the person support apparatus of FIG. 1.

A right head load cell (RHLC) 152a is illustratively positioned near the right head end of the person support apparatus 100 between a base support frame 106a secured to the base 106 near the head end 112 and the junction of the head end weigh frame member 134c and the right side weigh frame member 134a, as shown in the block diagram of FIG. 2. A left head load cell (LHLC) 152b is illustratively positioned near the left head end of the person support apparatus 100 between the base support frame 106a and the junction of the head end weigh frame member 134c and the left side weigh frame member 134b. A right foot load cell (RFLC) 152c is illustratively positioned near the right foot end of the person support apparatus 100 between a base support frame 106b secured to the base 106 near the foot end 114 of the person support apparatus 100 and the junction of the foot end weigh frame member 134d and the right side weigh frame member 134a. A left foot load cell (LFLC) 152d is illustratively positioned near the left foot end of the person support apparatus 100 between the base support frame 106b and the junction of the foot end weigh frame member 134d and the left side weigh frame member 134b. In the embodiment depicted in FIG. 2, the four corners of the person support deck 136 are shown extending beyond the four corners of the weigh frame 134, and hence beyond the positions of the four load cells 152a-152d.

In the illustrated embodiment, each of the load cells 152a-152d are weight sensors comprising resistive strain gauges coupled to a deflectable block (not shown), and structurally couple the weigh frame 134 to the base 106. It will be appreciated, however, that, alternatively, other weight detection devices may be used. Such devices may include, but are not limited to, linear variable displacement transducers (LVDTS) and/or other weight detection devices operable in accordance with known capacitive, inductive, or other physical principles.

In various embodiments, the load cells 152a-152d generate a signal which is transmitted to the computing device 200. In other words, the load cells 152a-152d generate load cell data that is transmitted to the computing device 200. As will be described in greater detail below, the computing device 200 receives the load cell data and, using a load pattern analysis module 301, may analyze the load cell data (e.g., waveforms) received from the load cells 152a-152d in order to detect or confirm a patient turn. For example, the load pattern analysis module 301 may determine that a particular waveform is indicative of a possible patient turn, since the signal generated by the load cells 152a-152d will vary as the patient moves from an initial position (i.e., a supine position) to a position in which they increase the amount of weight supported on one side of the person support surface 104, to a final position (i.e., a prone position).

Returning to FIG. 1, in various embodiments, the person support apparatus 100 further includes a mechanical sensor 154 coupled to the computing device 200. The mechanical sensor 154 may be, for example, a motion sensor, such as in the form of a pressure gauge (e.g., a piezoelectric sensor) or a strain gauge. The mechanical sensor 154 detects one or more physiological characteristics of an individual without contacting or viewing the individual or clothes that the individual is wearing. The mechanical sensor 154 is positioned below the person support surface 104 and is configured to sense breathing- and heartbeat-related motion (e.g., respiration rate data and heart rate data) of the individual. In some embodiments, the mechanical sensor 154 may be incorporated into the person support surface 104. Although positioned in FIG. 1 to correspond to an area below an abdomen or chest of an individual supported by the person support apparatus 100, it is contemplated that in some embodiments, the mechanical sensor 154 may be positioned in an area corresponding to the legs of the individual. For some applications, such positioning may provide a clearer pulse signal as compared to positioning below the chest or abdomen of the individual. In some embodiments, the mechanical sensor 154 includes a plurality of pressure or strain gauge sensors arranged in a grid. The use of a grid, rather than a single gauge, may enable improved signal reception. It is further contemplated that in some embodiments, a fiber optic sensor may be used as an alternative to the mechanical sensor 154.

Regardless of the specific type of mechanical sensor 154, in various embodiments, the mechanical sensor 154 senses motion of an individual disposed on the person support apparatus, such as motion resulting from the individual being turned by a caregiver or otherwise being repositioned, and generates a corresponding output. In embodiments, the output generated by the mechanical sensor 154 is transmitted to the computing device 200, which processes the output, including, for example, amplifying the output.

Figure 3:
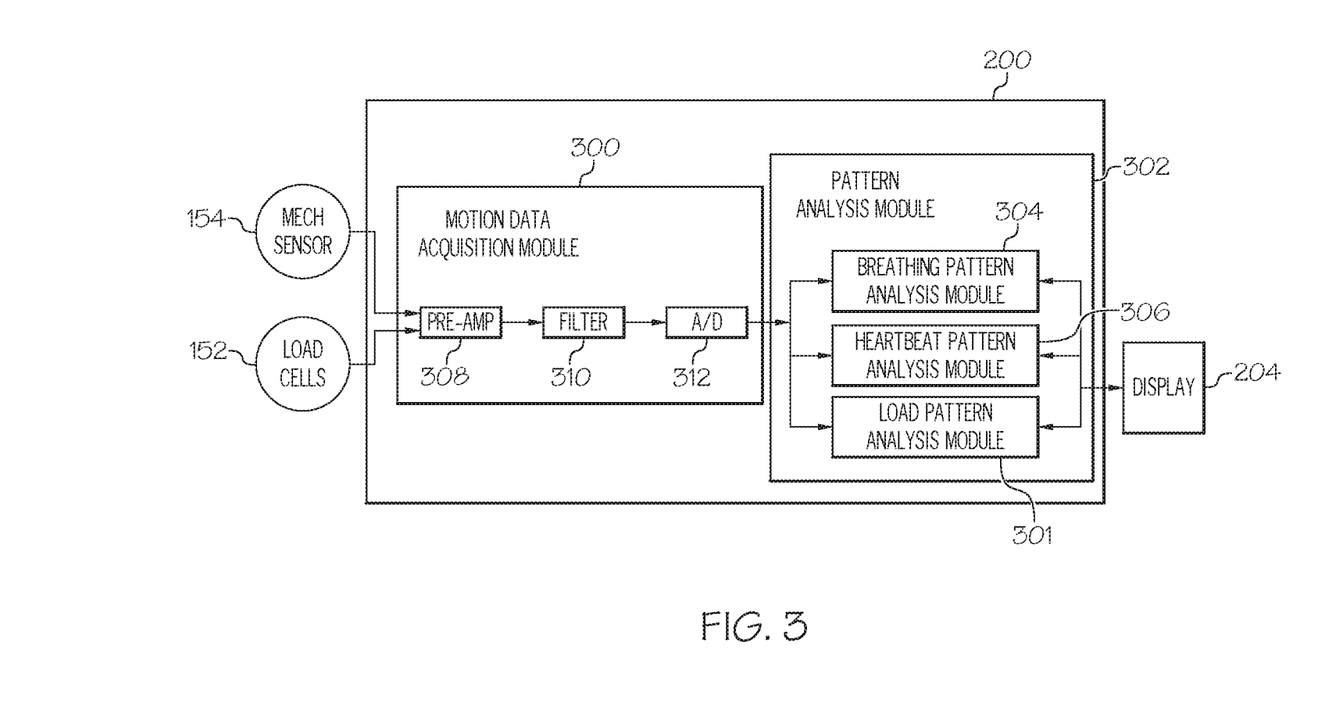
FIG. 3 is a block diagram illustrating an example control unit for a mechanical sensor for sensing breathing- and heartbeat-related motion in an individual according to one or more embodiments shown and described herein.

FIG. 3 is a schematic block diagram illustrating components of the computing device 200. In various embodiments, the computing device 200 includes a motion data acquisition module 300 and a pattern analysis module 302. The pattern analysis module 302 includes at least a load pattern analysis module 301, a breathing pattern analysis module 304 and a heartbeat pattern analysis module 306. However, in some embodiments, the pattern analysis module 302 may further include one or more of a cough analysis module, a restlessness analysis module, and a blood pressure analysis module (not shown). It is contemplated that other analysis modules may be included, depending on the particular embodiment.

In various embodiments, the motion data acquisition module 300 is adapted to non-invasively monitor repositioning, breathing, and heartbeat patterns of an individual supported on the person support apparatus 100. The load pattern analysis module 301, the breathing pattern analysis module 304, and the heartbeat pattern analysis module 306 are adapted to analyze the respective patterns in order to (a) predict an approaching clinical event, such as an asthma attack or heart condition-related lung fluid buildup, and/or (b) monitor the severity and progression of a clinical event as it occurs. In some embodiments, the load pattern analysis module 301, the breathing pattern analysis module 304, and the heartbeat pattern analysis module 306 are adapted to analyze the respective patterns in order to determine a likelihood of an approaching adverse clinical event without necessarily identifying the nature of the event. In the various embodiments described herein, the computing device 200 may provide a notification regarding the predicted or occurring clinical event to a caregiver via one of the user interfaces described herein.

The motion data acquisition module 300 typically includes circuitry for processing the raw signal generated by the load cells 152a-152d and the mechanical sensor 154, such as at least one pre-amplifier 308, at least one filter 310, and an analog-to-digital (A/D) converter 312. The filter 310 may be a band-pass or a low-pass filter. The low-passed data may be digitized at an appropriate sampling rate (e.g., 10 Hz) and stored in memory. After the A/D converter 312 converts the amplified and filtered signal, it is passed to the pattern analysis module 302 for analysis.

In some embodiments, the pattern analysis module 302 combines parameter data generated from the load pattern analysis module 301, the breathing pattern analysis module 304, and the heartbeat pattern analysis module 306, and analyzes the combined data in order to predict and/or monitor a clinical event or a patient turn, as will be described in greater detail below. For some embodiments, the pattern analysis module 302 derives a score for each parameter based on the parameter's deviation from baseline values (either for the individual or based on population averages). The pattern analysis module 302 may combine the scores, such as by taking an average, a maximum, a standard deviation, or another function of the scores. The combined score may then be compared to one or more threshold values to determine whether an event is predicted, currently occurring, or neither predicted nor occurring, and/or to monitor the severity and progression of an occurring event. In some embodiments, the pattern analysis module 302 may learn the criteria and/or functions for combining the individual parameter scores for the individual or patient group based on personal history. For example, the pattern analysis module 302 may perform such learning by analyzing parameters measured prior to previous clinical events and stored in the individual electronic medical records (EMR).

The breathing pattern analysis module 304 is adapted to extract breathing patterns from the motion data, and the heartbeat pattern analysis module 306 is adapted to extract heartbeat patterns from the motion data, while the load pattern analysis module 301 is adapted to extract repositioning patterns from the load cell data. In some embodiments, the load pattern analysis module 301 may additionally or alternatively extract repositioning patterns from the motion data received from mechanical sensor 154.

In embodiments, the load pattern analysis module 301 may determine that a particular waveform (i.e., signal) is indicative of a possible patient turn, since the signal generated by the load cells 152a-152d will vary as the patient moves from an initial position (i.e., a supine position) to a position in which they increase the amount of weight supported on one side of the person support surface 104, to a final position (i.e., a prone position).

In some embodiments, the individual's respiration rate is measured over a period of time, and the breathing pattern analysis module 304 determines a parameter of the individual's respiration rate over the time duration, such as the median respiration rate, the mean respiration rate, the maximum respiration rate, and/or a respiration rate pattern. The breathing pattern analysis module 304 may compare the predetermined parameter to the same parameter as determined on a previous day during a time period corresponding to the time period based upon which the parameter of respiration was determined on the present day. For example, the parameter may be compared to the same parameter as determined on a previous day for the same time duration and at the same time of day.

In various embodiments, the heartbeat pattern analysis module 306 applies a generally similar analysis to the individual's heart rate to that described with respect to the breathing pattern analysis module 304. For example, the heartbeat pattern analysis module 306 may compare a predetermined parameter of the individual's cardiac cycle to the same parameter as determined on a previous day during a time period corresponding to the time period based upon which the parameter of the cardiac cycle was determined on the present day in order to determine whether an event is predicted, currently occurring, or neither predicted nor occurring, and/or to monitor the severity and progression of an occurring event.

Although in embodiments, the computing device 200 is described as receiving or collecting information from the mechanical sensor 154 and the load cells 152a-152d, it is contemplated that any number of separate computing devices may be employed. For example, the mechanical sensor 154 may be communicatively coupled to one computing device while the load cells 152a-152d are communicatively coupled to a second computing device, with each computing device performing pattern analysis on the data it receives. Moreover, it should be understood that additional and/or alternative inputs may be employed depending on the particular embodiment. For example, in some embodiments, the person support surface 104 may include one or more pressure sensors that can detect movement of a patient based on a redistribution of pressure over the person support surface 104. Such systems may be used for predicting egress of an individual from the person support apparatus 100, and the data may be additionally analyzed to detect or confirm a patient turn. Additional details on systems for use in predicting egress may be found in U.S. Pat. No. 9,761,109, entitled "Occupant Egress Prediction Systems, Methods, and Devices," the entire contents of which is hereby incorporated by reference.

In various embodiments, the pattern analysis module 302, the load pattern analysis module 301, the breathing pattern analysis module 304, and/or the heartbeat pattern analysis module 306 may detect a possible patient turn and/or confirm the existence of a patient turn based on the signal from the load cells 152a-152d and/or the mechanical sensor 154. Additional details on the mechanical sensor 154 and the pattern analysis module 302 may be found, for example, in U.S. Pat. No. 8,491,492, entitled "Monitoring a Condition of a Subject," the entire contents of which is hereby incorporated by reference. Without being bound by theory, it is believed that a patient turn will decrease the respiration rate of the individual and increase the heart rate of the individual over a predetermined period of time as compared to a previous period of time. Accordingly, the pattern analysis module 302 may analyze the movement, the heart rate and the respiration rate of an individual and determine that a patient turn may have occurred when a heart rate increase in combination with a respiration rate decrease occurs over a predetermined time period along with a particular load cell waveform.

Figure 4:
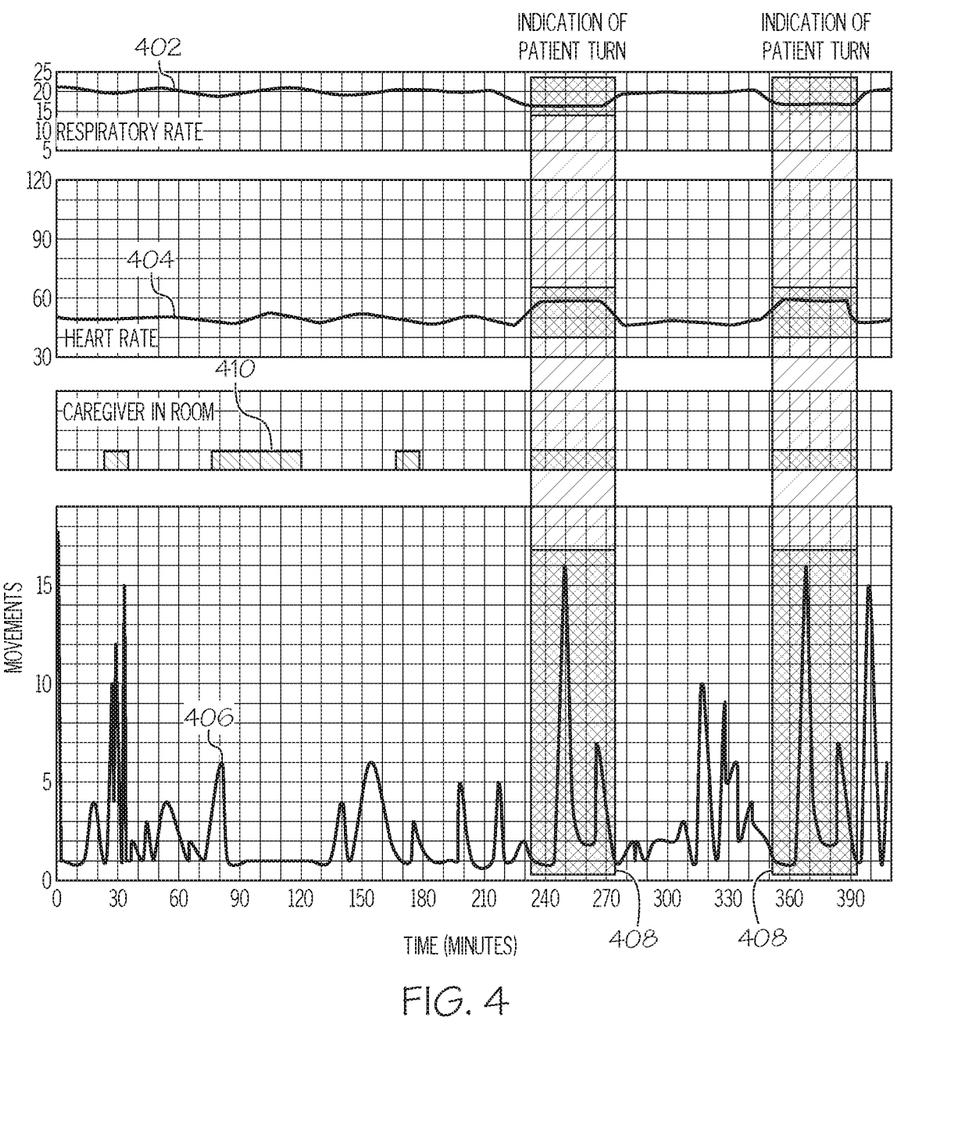
FIG. 4 is a graph plotting the respiratory rate, heart rate, location of a caregiver, and load cell data as a function of time to indicate the occurrence of a patient turn according to one or more embodiments shown and described herein.

For example, as shown in FIG. 4, the graphical plotting of the respiration rate 402, heart rate 404, and load cell data 406 over time (x-axis) each indicate a change at a particular time indicative of a patient turn. By combining the pattern analysis of the load cell data with the pattern analysis of the heart rate and respiration rate, the occurrence of a patient turn 408 can reliably be identified based on the data as compared to analysis of a pattern of any of the individual data sets alone. FIG. 4 also includes information regarding the presence of a caregiver 410 in the room, which may be used to further confirm the occurrence of a patient turn, as will now be described.

Caregiver Tracking System

Figure 5:
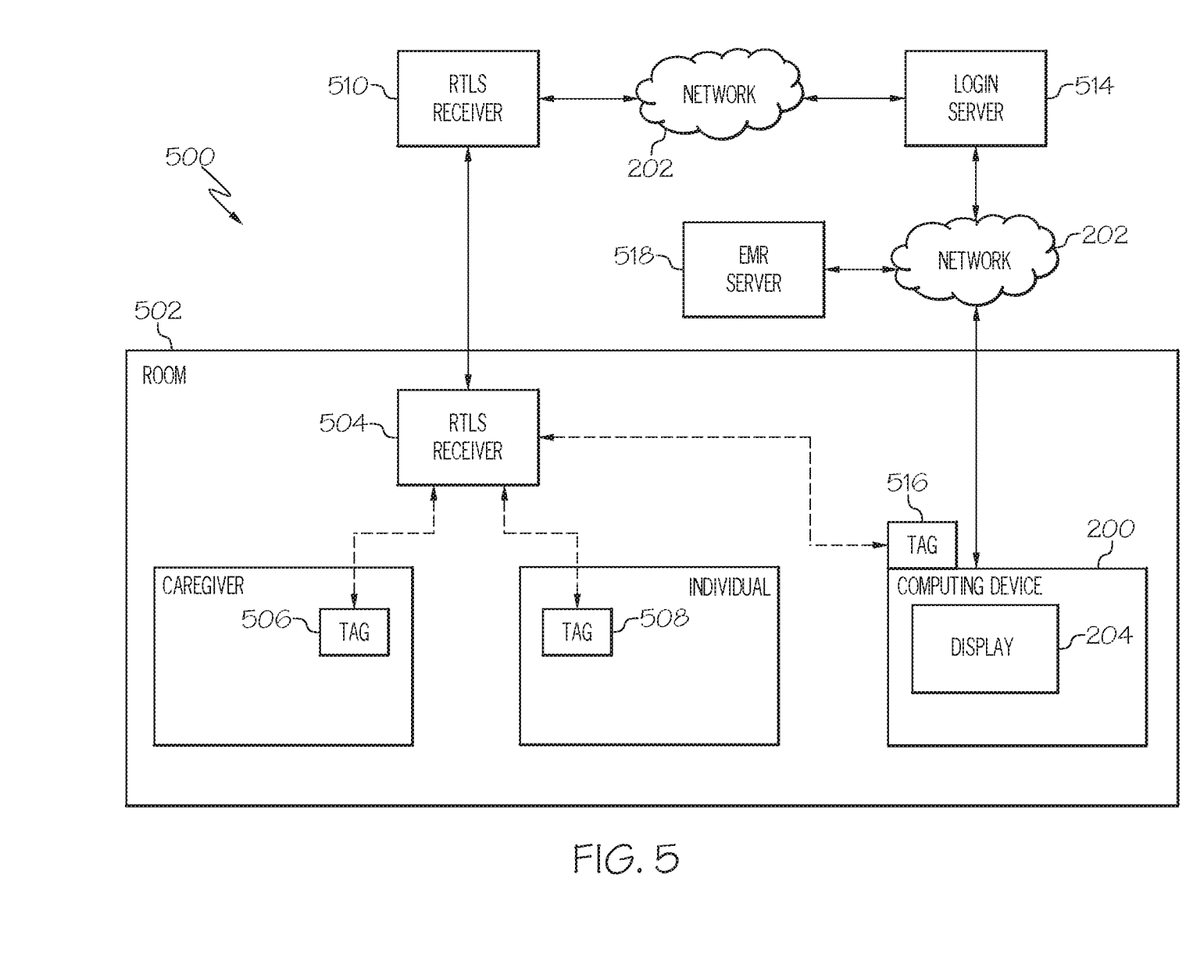
FIG. 5 is a block diagram showing an individual and a caregiver being located in a room and having tags communicating with a real time locating system (RTLS) according to one or more embodiments shown and described herein.

In various embodiments, a real time locating system 500 is provided for tracking various persons throughout an environment, such as a healthcare facility such as a hospital, nursing home, rehabilitation facility, doctor's office, or the like. In particular, the system 500 can detect the presence of one or more persons in a room 502. Accordingly, the real time locating system 500 can be used to determine if a caregiver is within a predetermined distance of the person support apparatus 100 during a detected patient turn.

The system 500 includes a real time locating system (RTLS) receiver 504 located within the room 502 to receive wireless signals from a token or tag 506 of a caregiver and from a token or tag 508 of an individual, such as a person disposed on the person support apparatus. The tags 506, 508 are carried by the caregiver and individual, respectively, and may be clipped or otherwise attached to the caregiver or individuals clothing or the like. In some embodiments, the tags 506, 508 may be in the form of a wrist band, key fob, wireless phone, pendant, or the like.

The caregiver's tag 506 sends caregiver identification data (ID) to the RTLS receiver 504, and the individual's tag 508 sends identification data for the individual to the RTLS receiver 504. In various embodiments, the identification data may be transmitted by the tags 506, 508 at predetermined time intervals, such as, by way of example and not limitation, every three seconds or every thirty seconds. In other embodiments, the identification data may be transmitted by the tags 506, 508 in response to a signal received from the receiver 504 or other device. In such embodiments, the battery life of the tags 506, 508 may be conserved because transmission only occurs in response to a request from the receiver 504 in communicative proximity with the tags 506, 508.

The RTLS receiver 504 may be included as part of a transceiver in some embodiments. Accordingly, the double-headed dashed arrows between the tags 506, 508 and the RTLS receiver 504 in FIG. 5 indicate that bidirectional (e.g., two-way) communication may exist between the tags 506, 508 and the RTLS receiver 504. However, it should be understood that it is not necessary for the wireless communication technology for communications from the RTLS receiver 504 to the tags 506, 508 be the same as the wireless communication technology for communications from the tags 506, 508 to the RTLS receiver 504. In various embodiments, the wireless communication technology may be, for example, infrared (IR), radio frequency (RF), ultrasound (US), ultra-wide band (UWB), or ultra-low frequency (ULF), or another wireless communication technology. In embodiments, the RTLS receiver 504 may be included as part of a wireless access point (WAP) that communicates using WiFi technology.

The RTLS receiver 504 sends the received caregiver ID data and identification data for the individual to an RTLS server 510. In some embodiments, the RTLS receiver 504 may also transmit RTLS receiver ID and/or locator unit ID data to the RTLS server 510. The RTLS receiver ID data or location unit ID data correlates to the room 502 in which the RTLS receiver 504 or the location unit is located. Accordingly, the RTLS server 510 can associate the caregiver ID data from the tag 506, the identification data for the individual from the tag 508, and the room ID data from the RTLS receiver 504 with each other to indicate which caregiver and individual are in which room. It should be appreciated that various facilities have a multitude of rooms 502 with RTLS receivers 504 that are in communication with the RTLS server 510 to track the whereabouts of a plurality of caregivers and individuals throughout the facility. Thus, the tags 506, 508, the RTLS receivers 504, and the RTLS server 510 together are considered a real time locating system (RTLS).

In FIG. 5, the RTLS server 510 communicates through the network 202 with a login server 514. Although depicted in FIG. 5 as two servers performing separate functions, it is contemplated that in some embodiments, the functions performed by the RTLS server 510 and the functions performed by the login server 514 may be performed on a single server. That is, in some embodiments, the software controlling the locating and tracking functionality of the RTLS server and the software controlling the login functionality of the login server 514 may reside on a single server. It is further contemplated that the functions of the RTLS server 510 and/or the login server 514 may be performed by the computing device 200 described hereinabove. The server and/or computing device may further have the functionality of any other servers in the network 202 in the facility. Accordingly, the login server 514 and/or the RTLS server 510 may function as, by way of example and not limitation, a nurse call server, an admission/discharge/transfer (ADT) server, an electronic medical records (EMR) server 518, or a work flow server. Furthermore, although the double-headed arrow interconnecting the RTLS receiver 504 with the RTLS server 510 implies a connection that does not involve the network 202 (e.g., direct cabling between the RTLS receiver 504 and the RTLS server 510), it is contemplated that communication between the RTLS receiver 504 and the RTLS server 510 may include the infrastructure of the network 202.

As shown in FIG. 5, the login server 514 is coupled to the computing device 200 in the room 502 via the network 202. The computing device 200 includes a display 204. In some embodiments, an Internet Protocol (IP) address or a media access control (MAC) address of the computing device 200 correlates to the room 502 in which the computing device 200 is located. Thus, a database in the RTLS server 510 and/or the login server 514 stores information regarding the location of the computing device 200 based on the IP or MAC address of the computing device 200 as communicated to the login server 512 via the network 202. Alternatively or additionally, a tag 516 may be attached to the computing device 200. The tag 516 communicates with the RTLS server 510 via the RTLS receiver 504, as shown in FIG. 5. The use of the tag 516 to track the whereabouts of a particular computing device 200 may be particularly suitable for embodiments in which the computing device 200 is intended for transportation throughout a facility, such as a tablet computer or a computer on wheels.

In various embodiments, depending on the identity of the caregiver, as indicated by the caregiver identification data (ID) from the tag 506, and the identity of the individual, as indicated by the identification data for the individual from the tag 508, that are sensed by the RTLS receiver 504 to be in the room 502, the login server 514 sends one or more messages to the computing device 200 to automatically log the caregiver into the computing device 200 and to display an initial screen on the display 204. Thus, in embodiments, the caregiver does not need to enter any information at the computing device 200 to log into the computing device 200. In various embodiments described herein, logging into the computing device 200 is also considered to be logging into the network 202. Accordingly, once the caregiver is logged into the computing device 200, the caregiver is able to navigate to various software applications available on various computing devices and servers connected to the network 202, including the RTLS server 510, the login server 514, and an electronic medical record (EMR) server 518. Additional details on the RTLS system, including various functions that can be performed using the caregiver location tracking system described herein, may be found in U.S. Patent Application Publication No. 2017/0004259, entitled "Automatic Contextual Login Using Real Time Locating System Information," the entirety of which is hereby incorporated by reference.

The EMR server 518 stores the electronic medical records for each of the individuals in the facility. As described above, in various embodiments, data from the load cells 152a-152d, data from the mechanical sensor 154, information regarding clinical events, individual parameter events related to respiratory rate and/or heart rate, and possible or confirmed patient turns can be stored in the individual's EMR. In various embodiments, the presence of a caregiver in the room 502 during a possible patient turn may also be stored in the individual's EMR.

For example, as shown in FIG. 4, the presence of the caregiver 410 in the room 502 may be recorded over time. When the pattern analysis module 302 determines that the respiration rate, heart rate, and/or load cell data indicate a possible occurrence of a patient turn, the presence of the caregiver in the room may be used to confirm. In particular, if the pattern analysis module 302 determines that the respiration rate, heart rate, and/or load cell data indicate a possible occurrence of a patient turn, but the caregiver is not present in the room, the patient turn will not be logged and stored in the individual's EMR. However, if the pattern analysis module 302 determines that the respiration rate, heart rate, and/or load cell data indicate a possible occurrence of a patient turn, and the caregiver is present in the room, as shown in FIG. 4, the patient turn will be logged and stored in the individual's EMR. In embodiments, it is contemplated that the occurrence of a patient turn, after being identified by the pattern analysis module 302, may be automatically logged in an individual's EMR, as shown in FIG. 6, which may increase the accuracy of the EMR regarding patient turns.

In some embodiments, in order to ensure that patient turns are not erroneously logged into the individual's EMR, the computing device 200 may request a confirmation of the turn from the caregiver. For example, after identifying the possible occurrence of a patient turn, the computing device 200 may display a confirmation prompt on the display 204, requesting an input from the caregiver to confirm that the patient was turned. In embodiments, the caregiver may select a button, press a key, or otherwise provide an input confirming that the turn occurred prior to the patient turn being logged in the EMR. In some such embodiments, unconfirmed turns may additionally be stored in the EMR, such as with an indication that a possible patient turn was detected but not confirmed.

Figure 6:
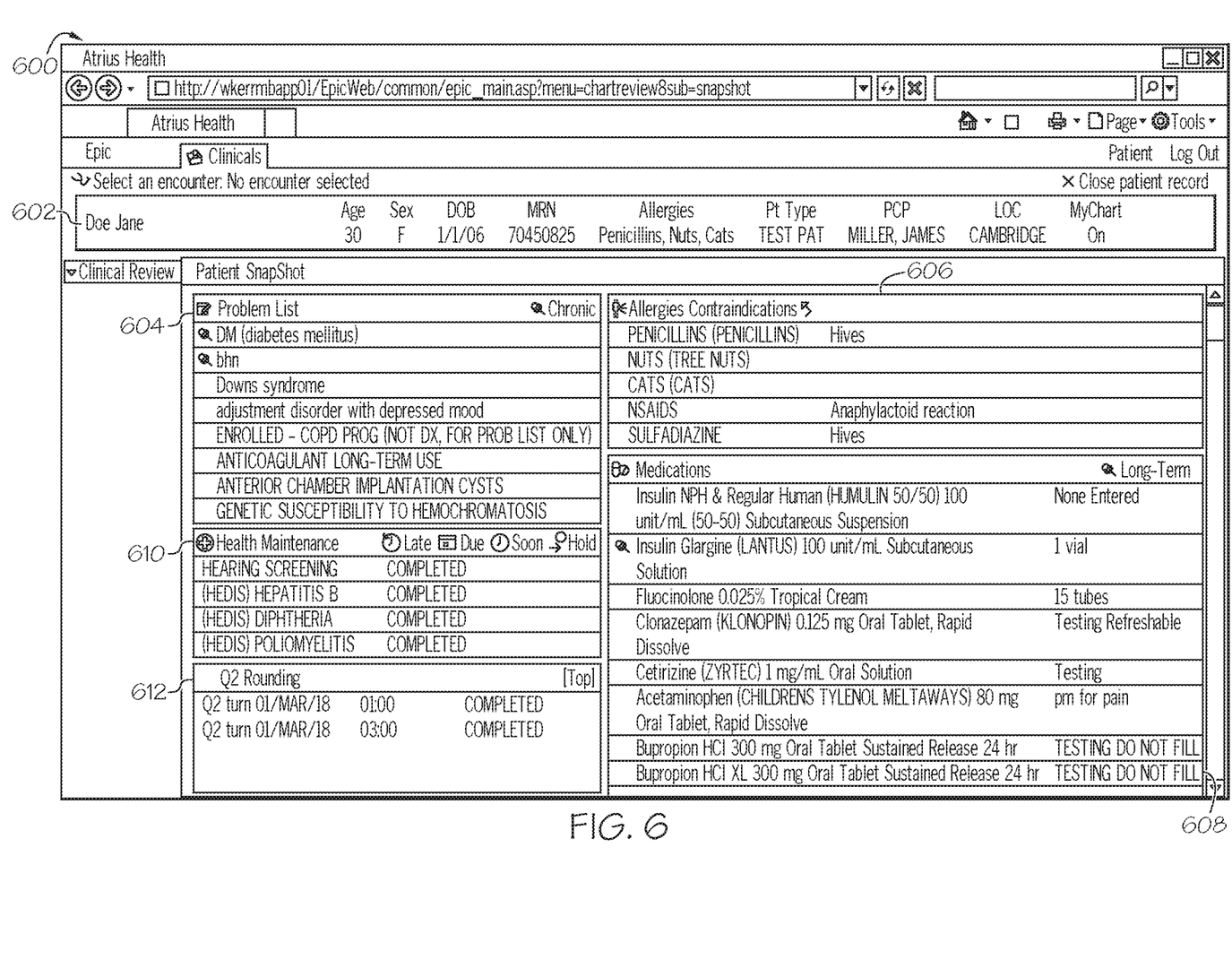
FIG. 6 is an example screenshot of an individual's electronic medical record (EMR) displayed on a computing device according to one or more embodiments shown and described herein.

FIG. 6 is a screenshot of an example individual's electronic medical record (EMR) 600, such as might be displayed on the display 204 of the computing device 200 when a caregiver is logged in. The EMR includes identification and demographic information 602, such as, by way of example and not limitation, the individual's name, age, sex, location, and the like. The EMR 600 shown in FIG. 6 also includes several additional blocks of information, including a problem list 604, an allergies/contraindications list 606, a medications list 608, a health maintenance log 610, and a turn log 612. It is contemplated that the EMR 600 may include any or all of these blocks of information, and that additional blocks of information may be included, depending on the particular embodiment. The problem list 604 may include, for example, diagnoses and conditions for which the individual is being treated. The allergies/contraindications list 606 may include any allergies of the individual, as well as a listing of any medications or procedures that are contraindicated based on other information available in the EMR.

The medications list 608 may include any medications the individual is taking or has taken, as well as information regarding dosage amount, time of last dosage, and the time for the next dosage. The health maintenance log 610 may include information regarding any procedures or treatments that have been performed on the individual. Finally, the turn log 612 may include a log of patient turns, such as those automatically identified and logged by the pattern analysis module 302 and/or turns entered manually by the caregiver. In embodiments, the turn log 612 includes the date and time that the turn was completed. In other embodiments, the turn log 612 may include information such as whether the turn was confirmed, the caregiver performing the turn, or additional notes from the caregiver regarding the turn. Accordingly, a user reviewing the individual's EMR can easily see the patient turn history for the individual, and can determine when the next turn should occur.

Figure 7:
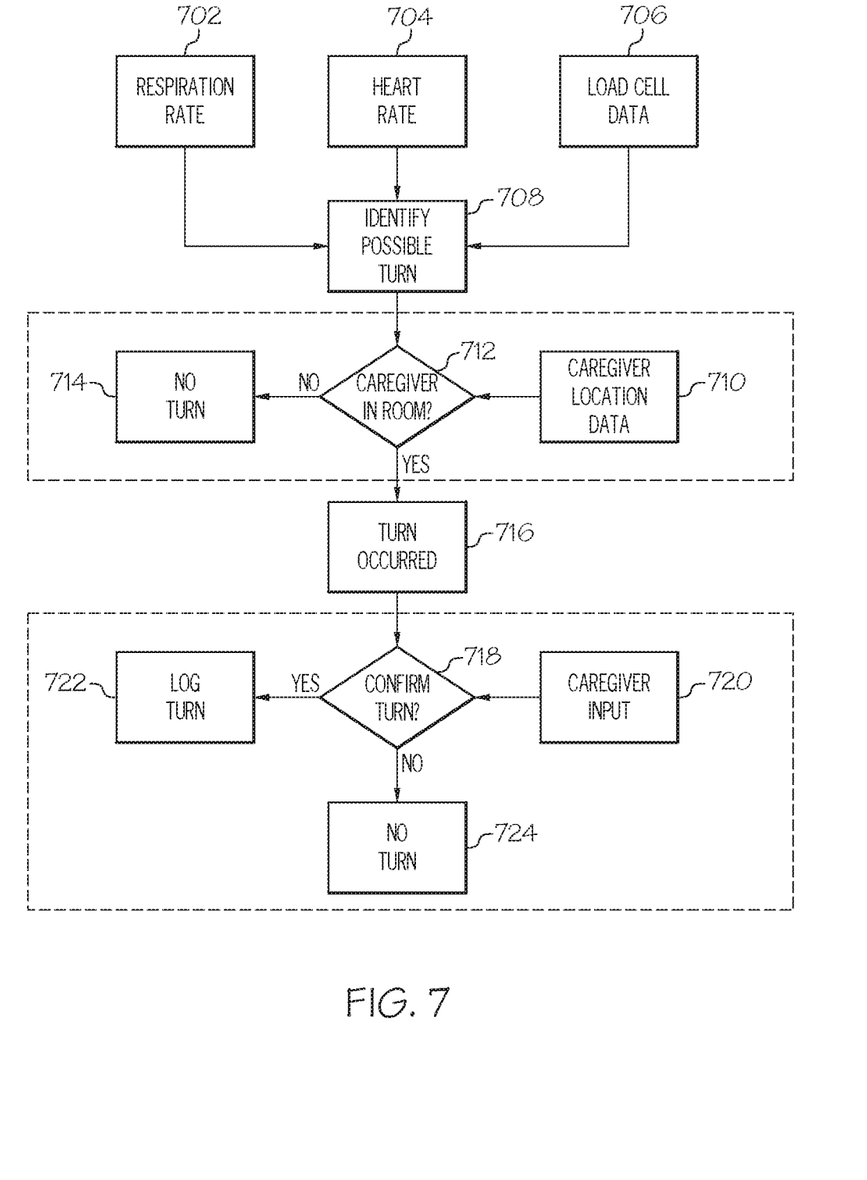
FIG. 7 is a block diagram of an example method for detecting and logging patient turns according to one or more embodiments shown and described herein.

In order to illustrate one or more embodiments in another way, FIG. 7 depicts an example flow chart showing a method of determining that a patient turn has occurred. First, an individual's respiration rate 702, heart rate 704, and load cell data 706 are analyzed to identify a possible turn at 708. For example, as described above, the pattern analysis module 302 on the computing device 200 can analyze the data received from the mechanical sensor 154 and the load cells 152a-152d, recognize that there has been a change in the individual's respiration rate, a change in the individual's heart rate, and that there has been movement on the patient support surface 104 indicative of a possible patient turn.

Next, in some embodiments, based on the caregiver location data 710, the computing device determines if the caregiver was in the room at 712. If the caregiver was not in the room at the time of the possible turn (e.g., a "no" at block 712), the computing device determines that no turn occurred at 714. However, if the caregiver was in the room at the time of the possible turn (e.g., a "yes" at block 712), the computing device determines that a turn occurred at 716. It should be understood that in embodiments, the use of caregiver location data to confirm the turn is optional. In embodiments not including such a step, but including a step of confirming the turn by requesting caregiver input, the method may proceed from block 708 to block 716.

In various embodiments, after determining that a turn occurred, the computing device may request confirmation that the turn occurred at 718. If, based on a received caregiver input 720 confirming the turn, the computing device confirms the turn (e.g., a "yes" at block 718), the turn is logged in the individual's EMR at 722. However, if the computing device cannot confirm the turn, such as from an indication from the caregiver that a turn did not occur or a lack of caregiver input (e.g., a "no" at block 718), the computing device determines that no turn occurred at 724. Alternatively, in some embodiments, if confirmation from the caregiver is not received, the computing device logs the turn in the individual's EMR with a notation that the turn was not confirmed.

Although the method shown in FIG. 7 is described as being performed by a computing device, it is contemplated that in some embodiments, more than one computing device or server communicatively coupled to the network 202 may perform one or more of the steps in the method. Accordingly, it should be understood that various facility information systems (e.g., the NaviCare® system from Hill-Rom, EMR systems, the Smart Connect® system from Hill-Rom, and the SmartSync® system from Hill-Rom) may communicate with one another in the various embodiments described herein to perform the functions described.

In some embodiments herein, in addition to determining that a patient turn has occurred and logging patient turns in the individual's EMR, the system described herein may provide a notification or a reminder to a caregiver that an individual should be turned. For example, the computing device 200 may display an alert or notification on the display 204 if a predetermined time period (e.g., a time period of greater than about an hour and 45 minutes, about two hours, about two hours and 15 minutes, or more) has passed since the last patient turn occurred. The particular time period can vary depending on the specific embodiment. Additionally, as an alternative to the computing device displaying an alert or notification, it is contemplated that any computing device connected to the network 202 can receive the alert or notification, including, for example, a mobile computing device carried by a caregiver, a computing device at a nurses' station, or the like. Furthermore, it is contemplated that any of the several computing devices and servers described in the various embodiments herein can determine that an alert or notification should be transmitted or displayed. For example, the pattern analysis module 302 can determine that the individual should be turned and that a turn has not occurred for the threshold time period, or an application or module on the EMR server 518, login server 514, RTLS server 510, or any other server or computing device connected to the network 202 can perform this function, provided that such server or computing device is communicatively coupled to the individual's EMR and can determine the time of the last logged patient turn.

In various embodiments, the patient turn data, and in particular, the occurrence of patient turns and the frequency thereof, can be used to adjust one or more treatment protocols in place for the individual and/or facility. For example, the data can be used to determine that certain groups of patients, such as based on age, sex, or diagnosis, should be turned more frequently. Accordingly, when trends based on the patient turn data indicate that certain groups of patients are more susceptible to a pressure ulcer, the threshold time period for an alert or notification may be adjusted to remind the caregiver to turn a particular individual more frequently. Patient turn data may further be used to confirm and document that certain treatment protocols are used, such as may be required by insurance or applicable regulations for the facility.

Accordingly, various embodiments described herein the system analyzes patterns in load cell data, heart rate data, and/or respiration rate data to determine if a patient turn occurred, and automatically logs the occurrence of the patient turn in the electronic medical record corresponding to an individual. Additional information, such as information regarding the location of a caregiver and/or an input from the caregiver can be used to confirm the occurrence of the patient turn. In various embodiments described herein, the system may further provide notifications or alerts or adjust treatment protocols based on the logged patient turns.

Many additional embodiments other than those described above are possible and still included in the spirit and scope of the claims defining the embodiments described herein. For example, although various combinations of features of a wound dressing have been shown and described, it is contemplated that these features may be combined in other ways described in detail or illustrated in the accompanying figures.

Embodiments can be described with reference to the following clauses, with preferred features laid out in the dependent clauses.

1. A system comprising: a person support apparatus comprising a person support surface and a support frame; a plurality of load cells for generating load cell data, at least one of the plurality of load cells being positioned at or proximate to each corner of the support frame; a sensor for sensing at least one of heart rate data and respiration rate data for an individual, the sensor disposed between the person support surface and the support frame; and a computing device coupled to the plurality of load cells and the sensor for receiving the load cell data and the at least one of heart rate data and respiration rate data for the individual, the computing device comprising a processor and memory storing computer readable and executable instructions that, when executed by the processor, cause the computing device to detect that a patient turn has occurred on the person support surface based on the load cell data and the at least one of heart rate data and respiration rate data for the individual, and cause an indication that the patient turn occurred to be logged in an electronic medical record corresponding to the individual.

2. The system of clause 1, wherein the executable instructions, when executed by the processor, further cause the computing device to request an input from the caregiver to confirm that the patient turn occurred.

3. The system of clause 1 or clause 2, wherein the computing device detects that the patient turn has occurred responsive to identifying a waveform in the load cell data indicative of a possible patient turn and at least one of an increase in heart rate and a decrease in respiration rate over a predetermined period of time.

4. The system of any of clauses 1-3, further comprising: a tag corresponding to a caregiver for sending caregiver identification data; a real time locating system (RTLS) receiver for receiving the caregiver identification data from the tag and transmitting the caregiver identification data; and a real time locating system (RTLS) server for receiving the caregiver identification data from the RTLS receiver and associating the caregiver identification data with a location of the RTLS receiver to indicate a location of the caregiver; wherein the executable instructions, when executed by the processor, further cause the computing device to confirm that the patient turn occurred based on the location of the caregiver.

5. The system of clause 4, wherein the computing device confirms that the patient turn occurred responsive to determining that the location of the caregiver is within a predetermined distance of the person support apparatus during the patient turn.

6. The system of any of clauses 1-5, wherein: the sensor senses heart rate data and respiration rate data for the individual; the computing device receives the heart rate data and the respiration rate data for the individual; and the computing device detects that the patient turn has occurred on the person support surface based on the load cell data, the heart rate data, and the respiration rate data for the individual.

7. The system of any of clauses 1-6, wherein the executable instructions, when executed by the processor, further cause the computing device to display an alert or notification indicative that a predetermined amount of time has passed since a patient turn occurred on a display of the computing device.

8. The system of clause 7, wherein the computing device displays the alert or notification responsive to a predetermined time period passing since a previous patient turn was logged in the electronic medical record corresponding to the individual.

9. A method comprising: receiving load cell data from a plurality of load cells positioned on a person support apparatus; receiving heart rate data and respiration rate data for an individual from a sensor coupled to the person support apparatus; determining that a waveform of the load cell data over a period of time is indicative of a possible patient turn; identifying at least one of a decrease in a respiration rate of the individual over the period of time and an increase in a heart rate of the individual over the period of time; determining that the patient turn occurred based on the determination that the waveform of the load cell data over a period of time is indicative of a possible patient turn and the identification of at least one of the decrease in the respiration rate and the increase in the heart rate of the individual over the period of time; and causing an indication that the patient turn occurred to be logged in an electronic medical record corresponding to the individual.

10. The method of clause 9, further comprising: receiving caregiver identification data indicative of a location of the caregiver; and confirming that the patient turn occurred based on the location of the caregiver.

11. The method of clause 10, wherein confirming that the patient turn occurred is responsive to determining that the location of the caregiver is within a predetermined distance of the person support apparatus during the patient turn.

12. The method of clause 11, wherein the predetermined distance is within a room in which the person support apparatus is located.

13. The method of any of clauses 9-12, further comprising causing an alert or notification indicative that a predetermined amount of time has passed since a patient turn occurred to be displayed on a display of a computing device.

14. The method of clause 13, wherein causing the alert or notification to be displayed is responsive to a predetermined time period passing since a previous patient turn was logged in the electronic medical record corresponding to the individual.

15. The method of clause 13 or clause 14, wherein the computing device is selected from the group consisting of a mobile computing device carried by a caregiver or a computing device at a nurses' station.

16. The method of any of clauses 9-15, further comprising requesting, from a caregiver, confirmation that the patient turn occurred prior to causing the indication that the patient turn occurred to be logged in the electronic medical record corresponding to the individual.

17. The method of clause 16, wherein, if confirmation from the caregiver is not received, the indication that the patient turn occurred is not logged in the electronic medical record corresponding to the individual.

18. The method of clause 16, wherein, if confirmation from the caregiver is not received, the indication that the patient turn occurred is logged in the electronic medical record corresponding to the individual with a notation that the patient turn was not confirmed.

19. The method of any of clauses 9-18, further comprising adjusting a treatment protocol based on a frequency of occurrence of patient turns logged in the electronic medical record corresponding to the individual.

20. The method of clause 19, wherein adjusting the treatment protocol comprises adjusting a threshold time period for an alert or notification regarding an upcoming patient turn for the individual.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. It should be understood that while the use of the word preferable, preferably or preferred in the description above indicates that the feature so described can be more desirable, it nonetheless cannot be necessary and embodiments lacking the same can be contemplated as within the scope of the disclosure, that scope being defined by the claims that follow.

In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It will be apparent to those skilled in the art that various modifications and variations can be made to the embodiments described herein without departing from the spirit and scope of the claimed subject matter. Thus it is intended that the specification cover the modifications and variations of the various embodiments described herein provided such modification and variations come within the scope of the appended claims and their equivalents.

What is claimed is:

1. A system comprising:
a person support apparatus comprising a person support surface and a support frame;
a plurality of load cells for generating load cell data, at least one of the plurality of load cells being positioned at or proximate to each corner of the support frame;
a sensor for sensing at least one of heart rate data and respiration rate data for an individual, the sensor disposed between the person support surface and the support frame; and
a computing device coupled to the plurality of load cells and the sensor for receiving the load cell data and the at least one of heart rate data and respiration rate data for the individual, the computing device comprising a processor and memory storing computer readable and executable instructions that, when executed by the processor, cause the computing device to detect that a patient turn has occurred on the person support surface based on the load cell data and the at least one of heart rate data and respiration rate data for the individual, and cause an indication that the patient turn occurred to be logged in an electronic medical record corresponding to the individual,
wherein the computing device detects that the patient turn has occurred responsive to identifying a waveform in the load cell data indicative of a possible patient turn and at least one of an increase in the heart rate data and a decrease in the respiration rate data over a predetermined period of time.

2. The system of claim 1, wherein the executable instructions, when executed by the processor, further cause the computing device to request an input from the caregiver to confirm that the patient turn occurred.

3. The system of claim 1, further comprising:
a tag corresponding to a caregiver for sending caregiver identification data;
a real time locating system (RTLS) receiver for receiving the caregiver identification data from the tag and transmitting the caregiver identification data; and
a real time locating system (RTLS) server for receiving the caregiver identification data from the RTLS receiver and associating the caregiver identification data with a location of the RTLS receiver to indicate a location of the caregiver;
wherein the executable instructions, when executed by the processor, further cause the computing device to confirm that the patient turn occurred based on the location of the caregiver.

4. The system of claim 3, wherein the computing device confirms that the patient turn occurred responsive to determining that the location of the caregiver is within a predetermined distance of the person support apparatus during the patient turn.

5. The system of claim 1, wherein the executable instructions, when executed by the processor, further cause the computing device to display an alert or notification indicative that a predetermined amount of time has passed since a patient turn occurred on a display of the computing device.

6. The system of claim 5, wherein the computing device displays the alert or notification responsive to a predetermined time period passing since a previous patient turn was logged in the electronic medical record corresponding to the individual.

7. A method comprising:
receiving load cell data from a plurality of load cells positioned on a person support apparatus;
receiving heart rate data and respiration rate data for an individual from a sensor coupled to the person support apparatus;
determining that a waveform of the load cell data over a period of time is indicative of a possible patient turn;
identifying at least one of a decrease in a respiration rate of the individual over the period of time and an increase in a heart rate of the individual over the period of time;
determining that the patient turn occurred based on the determination that the waveform of the load cell data over a period of time is indicative of a possible patient turn and the identification of at least one of the decrease in the respiration rate and the increase in the heart rate of the individual over the period of time; and
causing an indication that the patient turn occurred to be logged in an electronic medical record corresponding to the individual.

8. The method of claim 7, further comprising:
receiving caregiver identification data indicative of a location of the caregiver; and
confirming that the patient turn occurred based on the location of the caregiver.

9. The method of claim 8, wherein confirming that the patient turn occurred is responsive to determining that the location of the caregiver is within a predetermined distance of the person support apparatus during the patient turn.

10. The method of claim 9, wherein the predetermined distance is within a room in which the person support apparatus is located.

11. The method of claim 7, further comprising causing an alert or notification indicative that a predetermined amount of time has passed since a patient turn occurred to be displayed on a display of a computing device.

12. The method of claim 11, wherein causing the alert or notification to be displayed is responsive to a predetermined time period passing since a previous patient turn was logged in the electronic medical record corresponding to the individual.

13. The method of claim 11, wherein the computing device is selected from the group consisting of a mobile computing device carried by a caregiver or a computing device at a nurses' station.

14. The method of claim 7, further comprising requesting, from a caregiver, confirmation that the patient turn occurred prior to causing the indication that the patient turn occurred to be logged in the electronic medical record corresponding to the individual.

15. The method of claim 14, wherein, if confirmation from the caregiver is not received, the indication that the patient turn occurred is not logged in the electronic medical record corresponding to the individual.

16. The method of claim 14, wherein, if confirmation from the caregiver is not received, the indication that the patient turn occurred is logged in the electronic medical record corresponding to the individual with a notation that the patient turn was not confirmed.

17. The method of claim 7, further comprising adjusting a treatment protocol based on a frequency of occurrence of patient turns logged in the electronic medical record corresponding to the individual.

18. The method of claim 17, wherein adjusting the treatment protocol comprises adjusting a threshold time period for an alert or notification regarding an upcoming patient turn for the individual.

19. A system comprising:
  a person support apparatus comprising a person support surface and a support frame;
  a plurality of load cells for generating load cell data, at least one of the plurality of load cells being positioned at or proximate to each corner of the support frame;
  a sensor for sensing at least one of heart rate data and respiration rate data for an individual, the sensor disposed between the person support surface and the support frame; and
  a computing device coupled to the plurality of load cells and the sensor for receiving the load cell data and the at least one of heart rate data and respiration rate data for the individual, the computing device comprising a processor and memory storing computer readable and executable instructions that, when executed by the processor, cause the computing device to detect that a patient turn has occurred on the person support surface based on the load cell data and the at least one of heart rate data and respiration rate data for the individual, and cause an indication that the patient turn occurred to be logged in an electronic medical record corresponding to the individual,
  wherein the executable instructions, when executed by the processor, further cause the computing device to confirm that the patient turn occurred responsive to determining that a location of a caregiver is within a predetermined distance of the person support apparatus during the patient turn, the predetermined distance being within a room in which the person support apparatus is located.

* * * * *